(12) United States Patent
Pintoffl

(10) Patent No.: US 10,146,908 B2
(45) Date of Patent: Dec. 4, 2018

(54) METHOD AND SYSTEM FOR ENHANCED VISUALIZATION AND NAVIGATION OF THREE DIMENSIONAL AND FOUR DIMENSIONAL MEDICAL IMAGES

(71) Applicant: General Electric Company, Schenectady, NY (US)

(72) Inventor: Klaus Pintoffl, Oberosterreich (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 282 days.

(21) Appl. No.: 14/989,972

(22) Filed: Jan. 7, 2016

(65) Prior Publication Data

US 2017/0199651 A1    Jul. 13, 2017

(51) Int. Cl.
| | |
|---|---|
| *G06F 19/00* | (2018.01) |
| *G06F 3/0488* | (2013.01) |
| *G06F 3/0481* | (2013.01) |
| *G16H 40/63* | (2018.01) |

(52) U.S. Cl.
CPC .......... *G06F 19/321* (2013.01); *G06F 3/0488* (2013.01); *G06F 3/04815* (2013.01); *G06F 19/00* (2013.01); *G16H 40/63* (2018.01)

(58) Field of Classification Search
CPC .. G06F 3/0416; G06F 3/04815; G06F 3/0488; G06F 19/321; G06F 19/3406; G06F 2203/04104; G06F 3/04886; G06T 7/0012
See application file for complete search history.

(56) References Cited

U.S. PATENT DOCUMENTS

| | | | | |
|---|---|---|---|---|
| 2006/0181548 | A1* | 8/2006 | Hafey | G16H 40/63 345/619 |
| 2010/0094132 | A1* | 4/2010 | Hansen | A61B 8/00 600/443 |
| 2014/0184547 | A1* | 7/2014 | Tokunaga | G09G 5/14 345/173 |
| 2015/0160844 | A1* | 6/2015 | Kim | A61B 8/463 715/798 |
| 2015/0206346 | A1* | 7/2015 | Oh | A61B 6/466 345/419 |

FOREIGN PATENT DOCUMENTS

WO    WO-2017036921 A1 *   3/2017   ............. G06F 19/26

* cited by examiner

*Primary Examiner* — Jeffrey A Gaffin
*Assistant Examiner* — Bille M Dahir
(74) *Attorney, Agent, or Firm* — McAndrews, Held & Malloy, Ltd.; Jacob Groethe; David Bates

(57) ABSTRACT

A processor receives a selection of an image display mode via a user input device. The image display mode defines a number of medical images for display. The processor configures a surface of a touch panel user input device to define a plurality of fields. Each of the plurality of fields corresponds with a different one of the medical images. The processor receives an input, via the touch panel user input device, which selects one of the plurality of fields of the surface of the touch panel user input device and commands the processor to manipulate a medical image corresponding with the selected one of the plurality of fields. The processor manipulates at least the medical image corresponding with the selected one of the plurality of fields at one or more display devices based at least in part on the input.

20 Claims, 9 Drawing Sheets

METHOD AND SYSTEM FOR ENHANCED VISUALIZATION AND NAVIGATION OF THREE DIMENSIONAL AND FOUR DIMENSIONAL MEDICAL IMAGES

FIELD

Certain embodiments relate to medical image manipulation. More specifically, certain embodiments relate to a method and system for enhanced visualization and navigation of three dimensional (3D) and four dimensional (4D) medical images by a dynamically configurable touch panel. The touch panel comprises a touch input surface that is configurable based on a selected image display mode to define fields, where each of the fields corresponds with a medical image presented at a display system.

BACKGROUND

Existing medical imaging modalities and medical workstations may be used to review medical image data, including 3D or 4D data. Navigating 3D or 4D image data with current medical imaging systems, however, may be cumbersome and error-prone. For example, typical 3D ultrasound systems include digital potentiometers that each uses a separate rotary encoder for image zoom, parallel shift, and X, Y, and Z plane rotation. The display of the ultrasound system may present image data in multiple planes or views, such as an A-plane, B-plane, C-plane, and/or rendered view. After selecting an appropriate plane or view presented at the display, an ultrasound operator may manually rotate one or more of the rotary encoders to manipulate the displayed image data. In some instances, the ultrasound operator may inadvertently select a wrong plane, rotate the wrong rotary encoder, or turn the rotary encoder in the wrong direction.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY

A system and/or method is provided for enhanced visualization and navigation of three dimensional (3D) and four dimensional (4D) medical images by a dynamically configurable touch panel, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION

Figure 1:
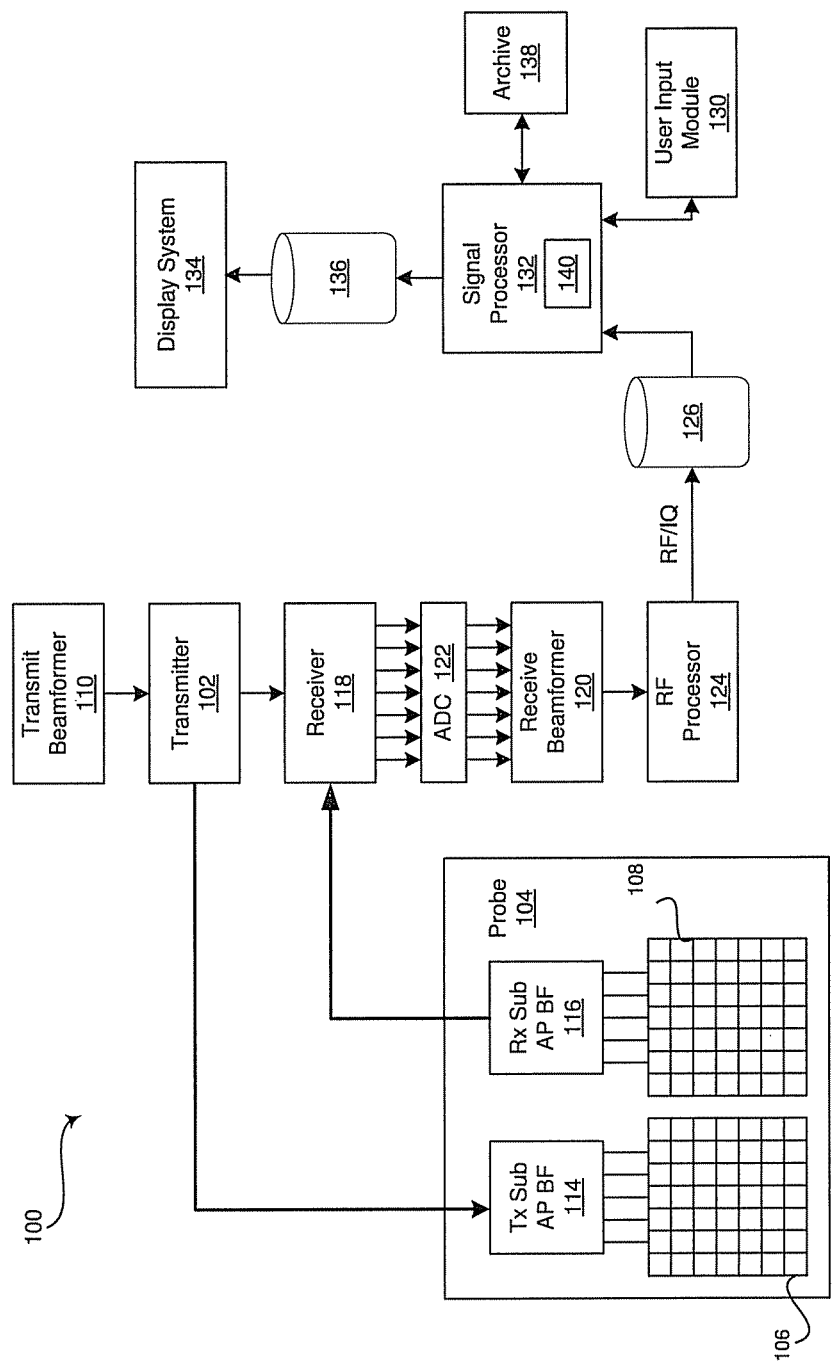
FIG. 1 is a block diagram of an exemplary ultrasound system that is operable to provide enhanced visualization and navigation of three dimensional (3D) and four dimensional (4D) medical images by a dynamically configurable touch panel, in accordance with various embodiments.

Certain embodiments may be found in a method and system for enhanced visualization and navigation of three dimensional (3D) and four dimensional (4D) medical images by a dynamically configurable touch panel. For example, various aspects have the technical effect of automatically and dynamically configuring a surface of a touch panel based on a selected image display mode to define fields that each corresponds with a medical image presented at a display system. Moreover, certain embodiments have the technical effect of facilitating a joint touch input and gesture at the configured touch panel for selecting a field of the touch panel corresponding with a medical image and providing a command for manipulating the medical image associated with the selected field.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to a medical imaging mode such as an ultrasound mode, a magnetic resonance mode, an x-ray mode, a computed tomography mode, etc. For example, an ultrasound mode may be a B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Moreover, although certain embodiments in the foregoing description may describe the imaging modality and/or images in the context of ultrasound, for example, unless so claimed, the scope of various aspects of the present invention should not be limited to ultrasound imaging modalities and images and may additionally and/or alternatively be applicable to any suitable medical imaging modality and image, such as computed tomography, magnetic resonance, x-ray, and the like.

Furthermore, the term processor or processing unit, as used herein, refers to any type of processing unit that can carry out the required calculations needed for various embodiments, such as single or multi-core: CPU, Graphics Board, DSP, FPGA, ASIC or a combination thereof.

It should be noted that various embodiments described herein that generate or form ultrasound images may include processing for forming images that in some embodiments includes beamforming and in other embodiments does not include beamforming. For example, an ultrasound image can be formed without beamforming, such as by multiplying the matrix of demodulated data by a matrix of coefficients so that the product is the image, and wherein the process does not form any "beams". Also, forming of ultrasound images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to provide enhanced visualization and navigation of three dimensional (3D) and four dimensional (4D) medical images by a dynamically configurable touch panel 130, in accordance with various embodiments. Referring to FIG. 1, there is shown an ultrasound system 100 comprising a transmitter 102, an ultrasound probe 104, a transmit beamformer 110, a receiver 118, a receive beamformer 120, a RF processor 124, a RF/IQ buffer 126, a user input module 130, a signal processor 132, an archive 138, an image buffer 136, and a display system 134.

The transmitter 102 may comprise suitable logic, circuitry, interfaces and/or code that may be operable to drive an ultrasound probe 104. The ultrasound probe 104 may comprise a one dimensional (1D, 1.25D, 1.5D or 1.75D) array, two dimensional (2D) array, or three dimensional (3D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure, and the like). The transmitted ultrasonic signals may be back-scattered from structures in the object of interest, like blood cells or tissue, to produce echoes. The echoes are received by the receive transducer elements 108. The group of receive transducer elements 108 in the ultrasound probe 104 may be operable to convert the received echoes into analog signals, undergo sub-aperture beamforming by a receive sub-aperture beamformer 116, and are then communicated to a receiver 118.

The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122. The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments, the plurality of A/D converters 122 may be integrated within the receiver 118.

The receive beamformer 120 may comprise suitable logic, circuitry, interfaces and/or code that may be operable to perform digital beamforming processing on the signals received from the plurality of A/D converters 122. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, input image acquisition and scan parameters, input settings, input configuration parameters, change a scan mode, select an image display mode, select a medical image for manipulation, manipulate medical image data, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, the archive 138, and/or the display system 134.

Figure 3:
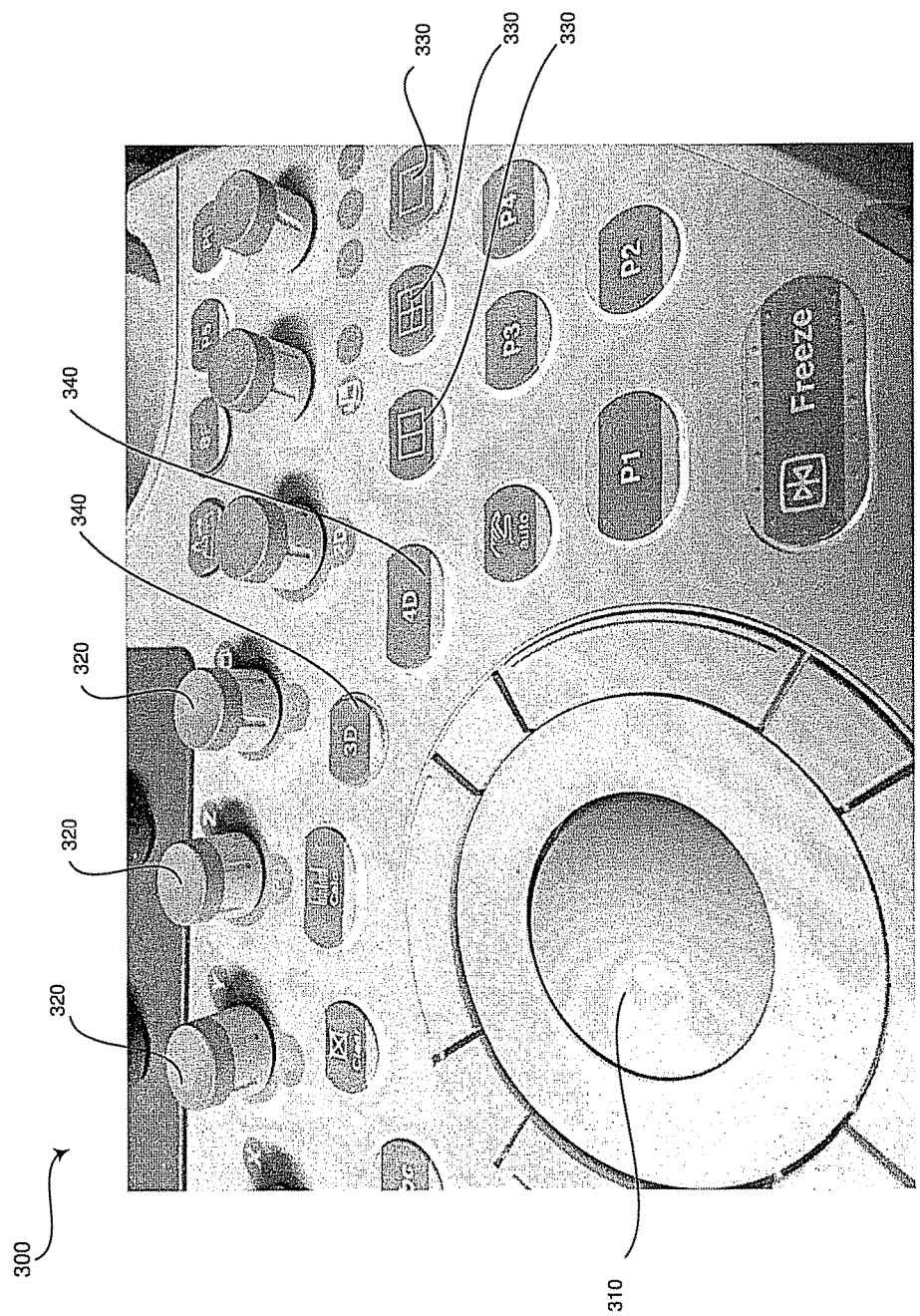
FIG. 3 illustrates an exemplary control panel of an ultrasound system, in accordance with exemplary embodiments.
Figure 4:
FIG. 4 illustrates an exemplary touch panel and display system of an ultrasound system or medical workstation, in accordance with certain embodiments.

In a representative embodiment, the user input module 130 may comprise an ultrasound system control panel 300 as illustrated in FIG. 3 and/or a touch panel 410 as illustrated in FIG. 4, for example. The user input module 130 may be operable to select an image acquisition or viewing mode, select an image display mode, activate touch panel 410 functionality, select a medical image for manipulation, and manipulate the medical image data, among other things. Referring to FIG. 3, an exemplary control panel 300 of an ultrasound system 100 may comprise a trackball 310, rotary encoders 320, image display mode buttons 330, acquisition/viewing mode buttons 340, and the like. The trackball 310 may be used to move objects on the display system 134 and can include buttons on either side for selecting functions, similar to a mousing device of a personal computer. The rotary encoders 320 may be rotatable to provide X-rotation, Y-rotation, Z-rotation, parallel shift, zoom, or any suitable functionality depending on a selected operating mode. In various embodiments, the rotary encoders may be depressible to enter a desired operating mode. For example, depressing the X-rotation rotary encoder 320, or any suitable user input module 130 selection component, may launch the touch panel functionality. The image display mode buttons 330 may be inputs for selecting a display mode, such as a single image view mode, a dual-view mode, a quad-view mode, or any suitable display mode for presenting one or more medical images. The acquisition/viewing mode buttons 340 may be operable to receive an acquisition/viewing mode selection, such as to acquire and/or view 3D image data or 4D image data.

Referring to FIG. 4, an exemplary touch panel 410 and display system 134 of an ultrasound system 100 or medical workstation 200 is provided, in accordance with certain embodiments. The display system 134 may be operable to display medical images in a selected display mode, such as a single image view mode, a dual-view mode, a quad-view mode, or any suitable display mode for presenting one or more medical images. The user input module 130 may comprise the touch panel 410 operable to select a displayed medical image for manipulation and manipulate the medical image data, for example. The touch panel 410 is a touch-driven interface such as a touch-screen or a touch-pad that may provide improved interaction with displayed information by reducing the number of steps it may take to accomplish the same interaction using a standard menu, rotary encoders, keyboard, and/or mouse. The touch panel 410 may sense inputs using a variety of techniques, such as heat, finger pressure, high capture rate cameras, infrared light, optic capture, and shadow capture, for example. In an exemplary embodiment, the touch panel 410 may be a multi-touch interface that allows for multiple simultaneous inputs. Certain embodiments utilize multi-touch interfaces to facilitate image manipulation, such as zooming and/or rotation, for example. As described in more detail below, the touch panel 410 is operable to receive a joint touch input and gesture. The touch input may select a field of the touch panel 410 corresponding with a medical image and the gesture may correspond with a command for manipulating the medical image associated with the selected field.

Referring again to FIG. 1, additionally and/or alternatively to the control panel 300 and touch panel 410 of FIGS. 3 and 4, the user input module 130 may comprise a mousing device, keyboard, remote control, switch, sliding bar, voice activated input, or any suitable device or mechanism operable to receive a user input. The user input module 130 may be integrated with other components, such as the ultrasound probe 104 or display system 134, or can be a separate component. For example, the display system 134 may be a touch-screen display that provides user input module 130 functionality.

The signal processor 132 may comprise suitable logic, circuitry, interfaces and/or code that may be operable to process the ultrasound scan data for generating an ultrasound image for presentation on a display system 134. The signal processor 132 is operable to perform one or more processing operations according to a plurality of selectable ultrasound modalities on the acquired ultrasound scan data. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. The processed image data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise an image manipulation module 140.

The ultrasound system 100 may be operable to continuously acquire ultrasound information at a frame rate that is suitable for the imaging situation in question. Typical frame rates range from 20-70 but may be lower or higher. The acquired ultrasound information may be displayed on the display system 134 at a display-rate that can be the same as the frame rate, or slower or faster. An image buffer 136 is included for storing processed frames of acquired ultrasound information that are not scheduled to be displayed immediately. Preferably, the image buffer 136 is of sufficient capacity to store at least several seconds worth of frames of ultrasound information. The frames of ultrasound information are stored in a manner to facilitate retrieval thereof according to its order or time of acquisition. The image buffer 136 may be embodied as any known data storage medium.

Figure 5:
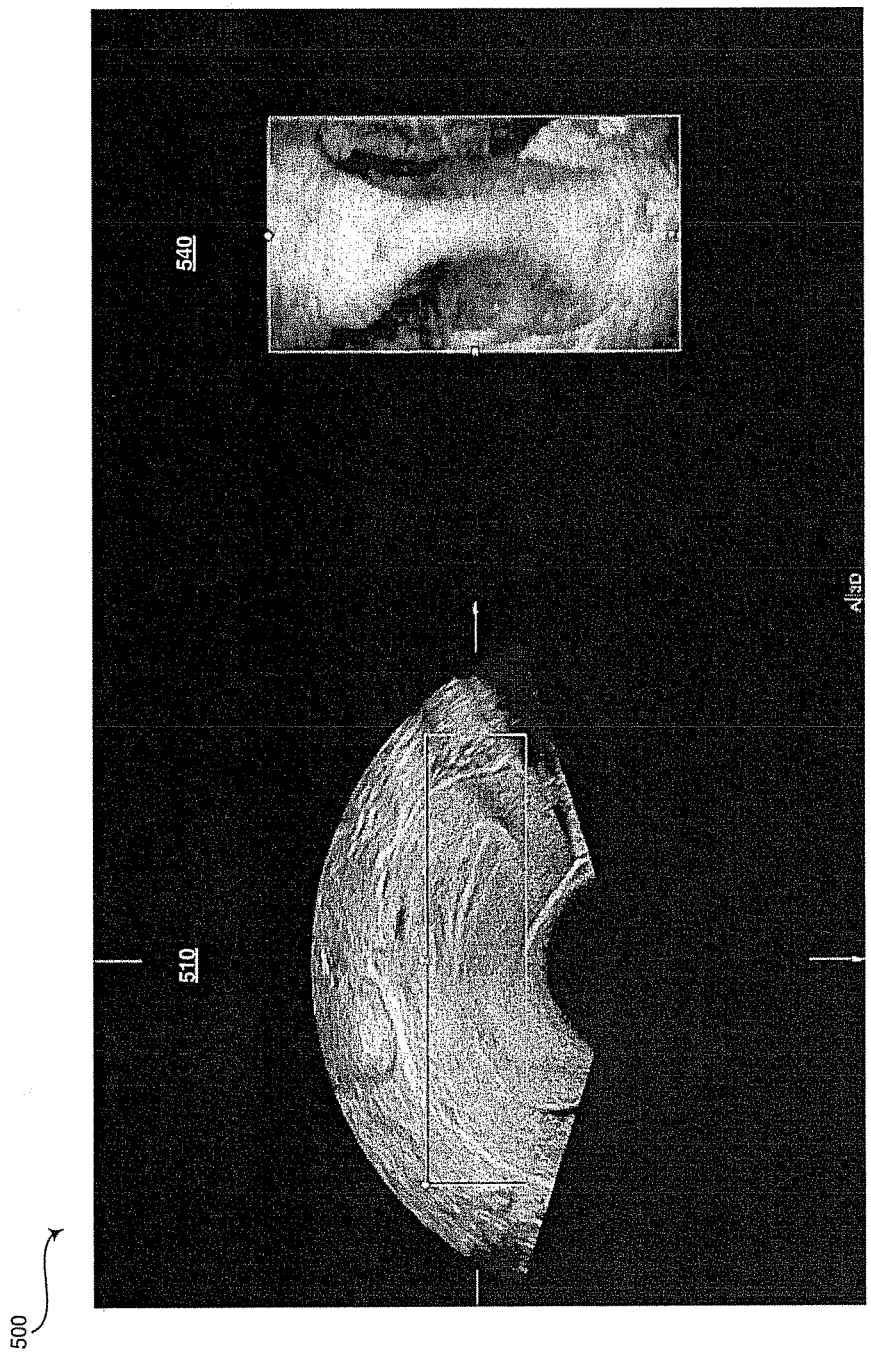
FIG. 5 is a screenshot of an exemplary dual-view image display mode, in accordance with an embodiment.
Figure 6:
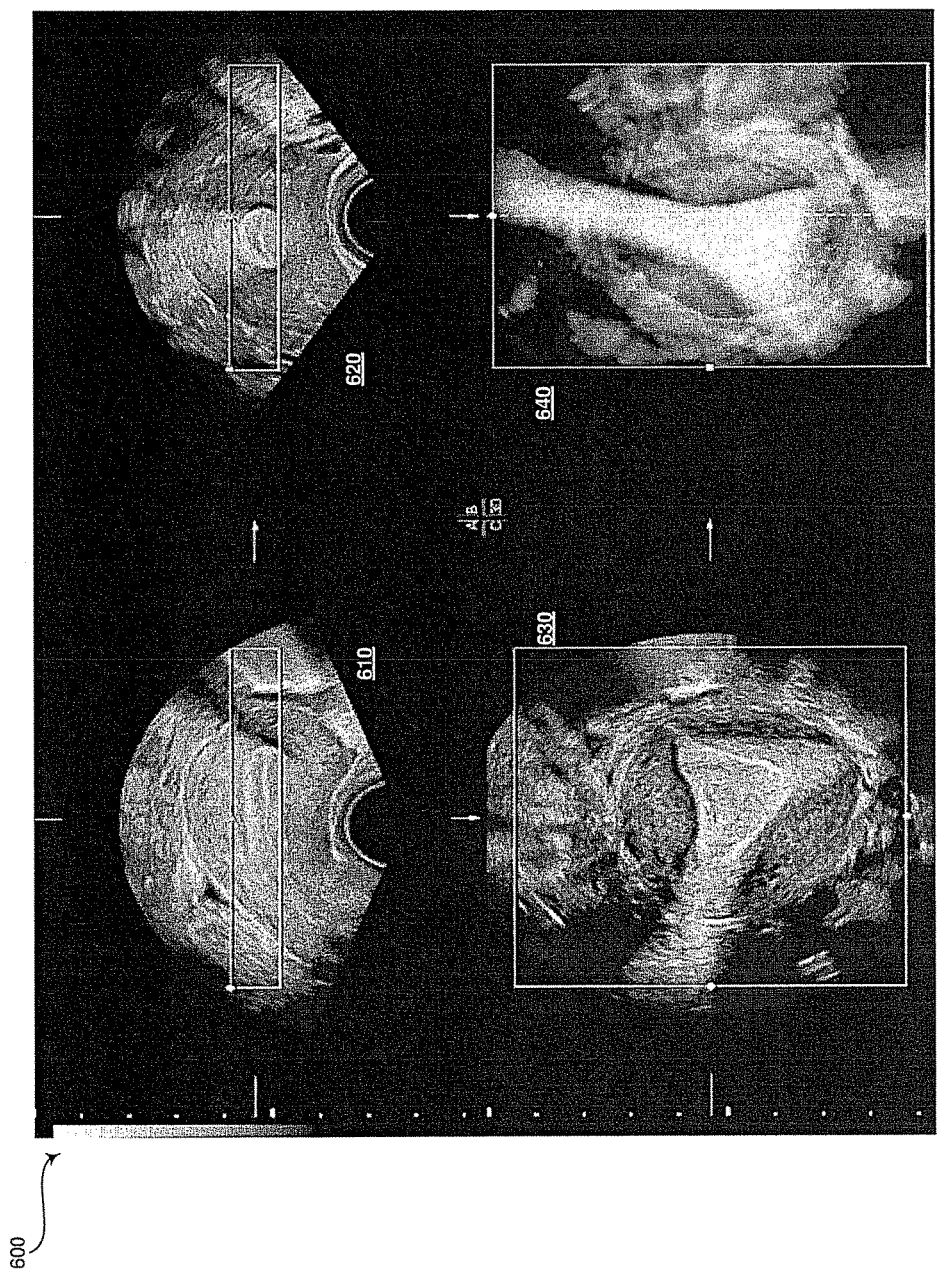
FIG. 6 is a screenshot of an exemplary quad-view image display mode, in accordance with an embodiment.
Figure 7:
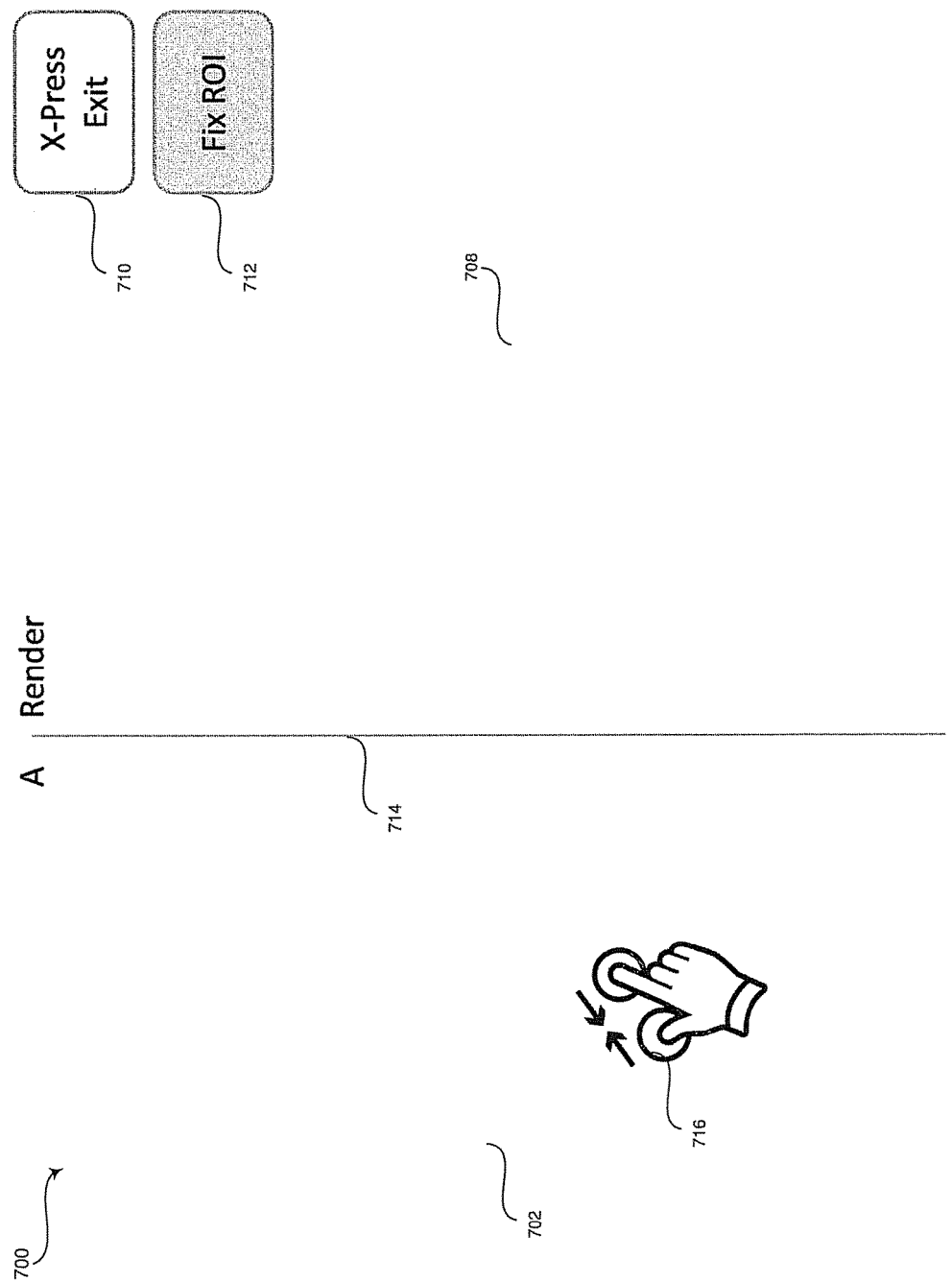
FIG. 7 illustrates an exemplary touch panel configured with fields corresponding with the dual-view image display mode of FIG. 5.
Figure 8:
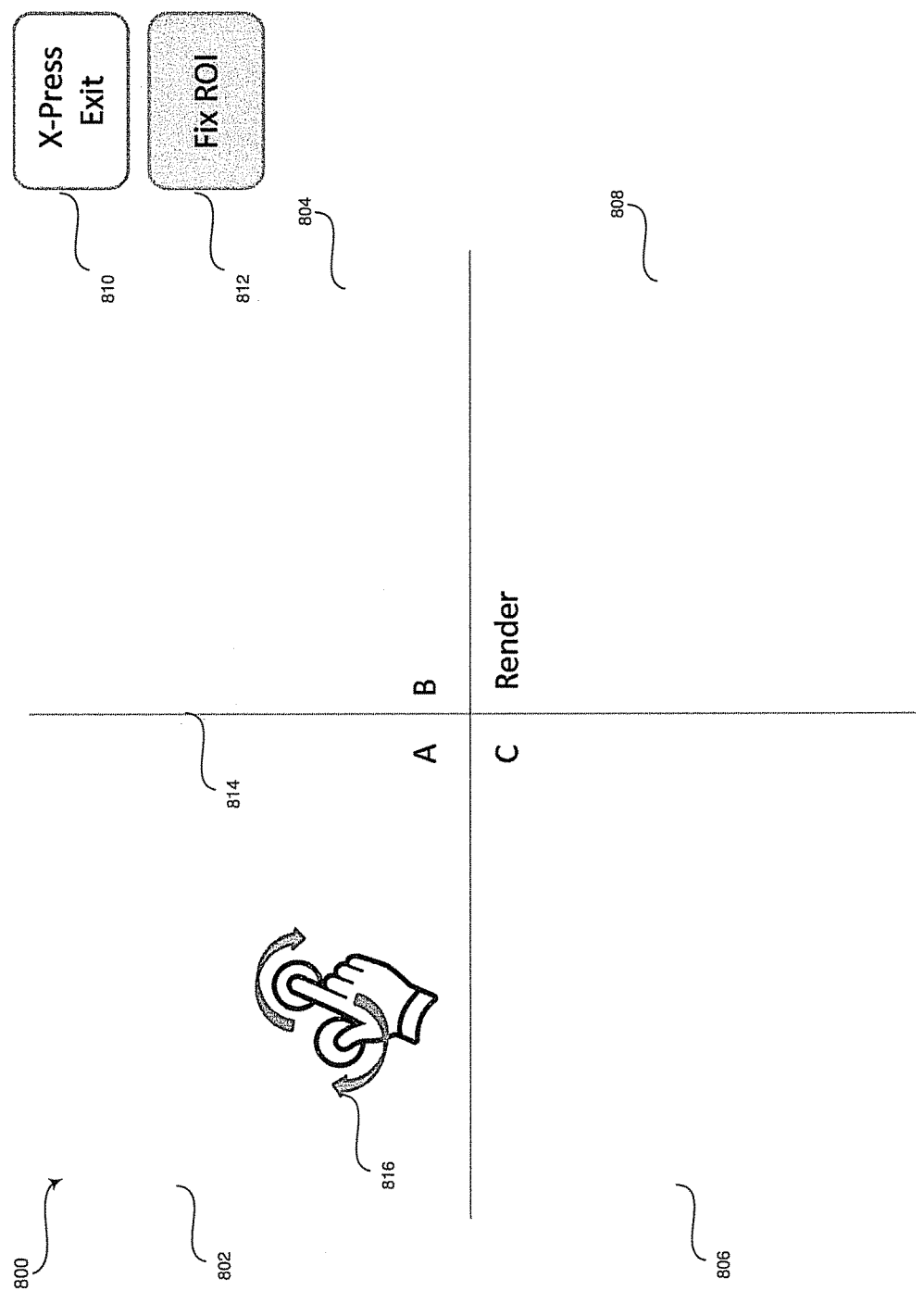
FIG. 8 illustrates an exemplary touch panel configured with fields corresponding with the quad-view image display mode of FIG. 6.

The image manipulation module 140 may comprise suitable logic, circuitry, interfaces and/or code that may be operable to dynamically configure a touch panel 410 to define fields on the surface of the touch panel 410 that correspond with the number of medical images displayed at a display system 134 based on a selected image display mode. The image manipulation module 140 may be operable to manipulate the displayed medical images based on a joint touch input and gesture. The term "joint" refers to a touch input and gesture provided at the surface of the touch panel 130, 410 without removing the input mechanism (e.g., finger(s) of a user, a stylus, etc.) from the surface of the touch panel 130, 410. In other words, the input continues for as long as at least a portion of the input mechanism maintains contact with the surface of the touch panel 130, 410. Once contact is completely broken from the input surface of the touch panel 130, 410, any subsequent contact is considered a separate input. The touch input received at the touch panel 410 may select a field of the touch panel 410 corresponding with a particular displayed medical image and the gesture provides the command for manipulating the medical image associated with the selected field. FIGS. 5 and 6 illustrate screenshots of exemplary medical images 510, 540, 610-640 that may be presented at a display system 134, touch panel 410, 700, 800, and/or any suitable display device, in a dual-view image display mode 500 and a quad-view image display mode 600 as described below. FIGS. 7 and 8 illustrate exemplary touch panel configurations with fields corresponding with the image display modes of FIGS. 5 and 6.

FIG. 5 is a screenshot of an exemplary dual-view image display mode 500, in accordance with an embodiment. FIG. 6 is a screenshot of an exemplary quad-view image display mode 600, in accordance with an embodiment. Referring to FIG. 5, the dual-view image display mode 500 comprises two medical images, which may be the A plane 510 and a rendered volume 540, for example. Referring to FIG. 6, the quad-view image display mode 600 comprises four medical images, which may be the A plane 610, B plane 620, C plane 630, and a rendered volume 640, for example. In various embodiments, the A plane 510, 610 may be the plane parallel to the acquisition plane. The B plane 620 may be perpendicular to the A plane 510, 610, but parallel to the ultrasound beam. The C plane 630 may be perpendicular to both the acquisition plane and the ultrasound beam. As an example, the A plane 510, 610 may be a midsagittal plane of a pelvic floor, the B plane 620 may be a coronal plane, and the C plane may be an axial plane. Although examples of specific imaging planes are presented, it should be understood that the imaging planes on 3D ultrasound can be varied in an arbitrary fashion to, for example, enhance the visibility of a given anatomical structure, either at the time of acquisition or offline at a later time. The one 510 or three 610, 620, 630 orthogonal images may be complemented by a rendered image 540, 640, which may be a semi-transparent representation of the voxels in a definable region of interest, for example. The dual-view image display mode 500 and quad-view image display mode 600 may be presented by the image manipulation module 140 at a display system 134, a touch panel 410, 700, 800, and/or at any suitable display device in response to a received image display mode selection.

FIG. 7 illustrates an exemplary touch panel 700 configured by the image manipulation module 140 to have fields 702, 708 corresponding with the dual-view image display mode 500 of FIG. 5. FIG. 8 illustrates an exemplary touch panel 800 configured by the image manipulation module 140 to have fields 802-808 corresponding with the quad-view image display mode 600 of FIG. 6. Referring to FIG. 7, the touch panel 700 comprises a surface having a first field 702 and a second field 708 separated by a dividing line 714 as defined by the image manipulation module 140 based on a received image display mode selection. The first 702 and second 708 fields are configured by the image manipulation module 140 to correspond with first 510 and second 540 medical images, respectively, presented on the touch panel 700 and/or at a display system 134. Referring to FIG. 8, the touch panel 800 comprises a surface having a first field 802, a second field 804, a third field 806, and a fourth field 808 separated by dividing lines 814 as defined by the image manipulation module 140 based on a received image display mode selection. The first 802, second 804, third 806, and fourth 808 fields are configured by the image manipulation module 140 to correspond with first 610, second 620, third 630, and fourth 640 medical images, respectively, presented on the touch panel and/or at the display system 134. The dividing line(s) 714, 814 may or may not be shown or presented on the touch panel 700, 800. In various embodiments, the medical images 510, 540, 610-640 may be displayed at the touch panel 700, 800 additionally and/or alternatively to presenting the images 510, 540, 610-640 at a display system 134. The touch panel 700, 800 may further comprise soft buttons 710, 712, 810, 812 that may be associated with pre-defined and/or user-defined functionality. For example, as illustrated in FIGS. 7 and 8, a first button 710, 810 may be associated with a mechanism for exiting the touch panel functionality. The second button 712, 812 can be associated with a mechanism for fixing or setting the region of interest so that the user joint touch input and gesture received at the touch panel 410, 700, 800 is applied to select and manipulate the presented image data. In certain embodiments, the touch panel 410, 700, 800 may have different functionality when the region of interest is not fixed and/or when the image selection and manipulation touch panel application is not active.

The touch panel 410, 700, 800 may be configured to receive touch inputs and/or gestures 716, 816. For example, the touch panel 410, 700, 800 may receive a stylus, one or more fingers of a user, or the like, as an input that is provided to the image manipulation module 140. The received input may cause the image manipulation module 140 to select a medical image 510, 540, 610-640 corresponding with the field 702, 708, 802-808 where the input was provided. Moreover, while the stylus, one or more fingers of a user, or the like remains in contact with the surface of the touch panel 410, 700, 800, the touch panel may receive a gesture 716, 816 that is provided to and translated by the image manipulation module 140 to manipulate the selected image 510, 540, 610-640. As an example, the user may slide the stylus or a finger left or right to rotate the selected image 510, 540, 610-640 about the Y-axis. As another example, the user may slide the stylus or a finger up or down to rotate the selected image 510, 540, 610-640 about the X-axis. In various embodiments, the image manipulation module 140 is configured to translate multi-touch gestures received at the touch panel 410, 700, 800. For example, moving two fingers apart or together 716 may zoom in or zoom out of the selected image 510, 540, 610-640. As another example, moving two fingers in a circular motion 816 may rotate the selected image 510, 540, 610-640 about the Z-axis. In an exemplary embodiment, the gesture input may extend into a neighboring field 702, 708, 802-808 of the touch panel 410, 700, 800 without changing the selection of the image 510, 540, 610-640. For example, after placing a finger in field 802 to select the first image 610 in the quad-view image display 600, a user may swipe their finger across into field 804 to rotate about the Y-axis or swipe down into fields 806 or 808 to rotate the selected image 610-640 about the X-axis. The user may remove the finger(s) or stylus from the surface of the touch panel 410, 700, 800 and provide an input at a different field 702, 708, 802-808 to select a different image 510, 540, 610-640 for manipulation.

Figure 2:
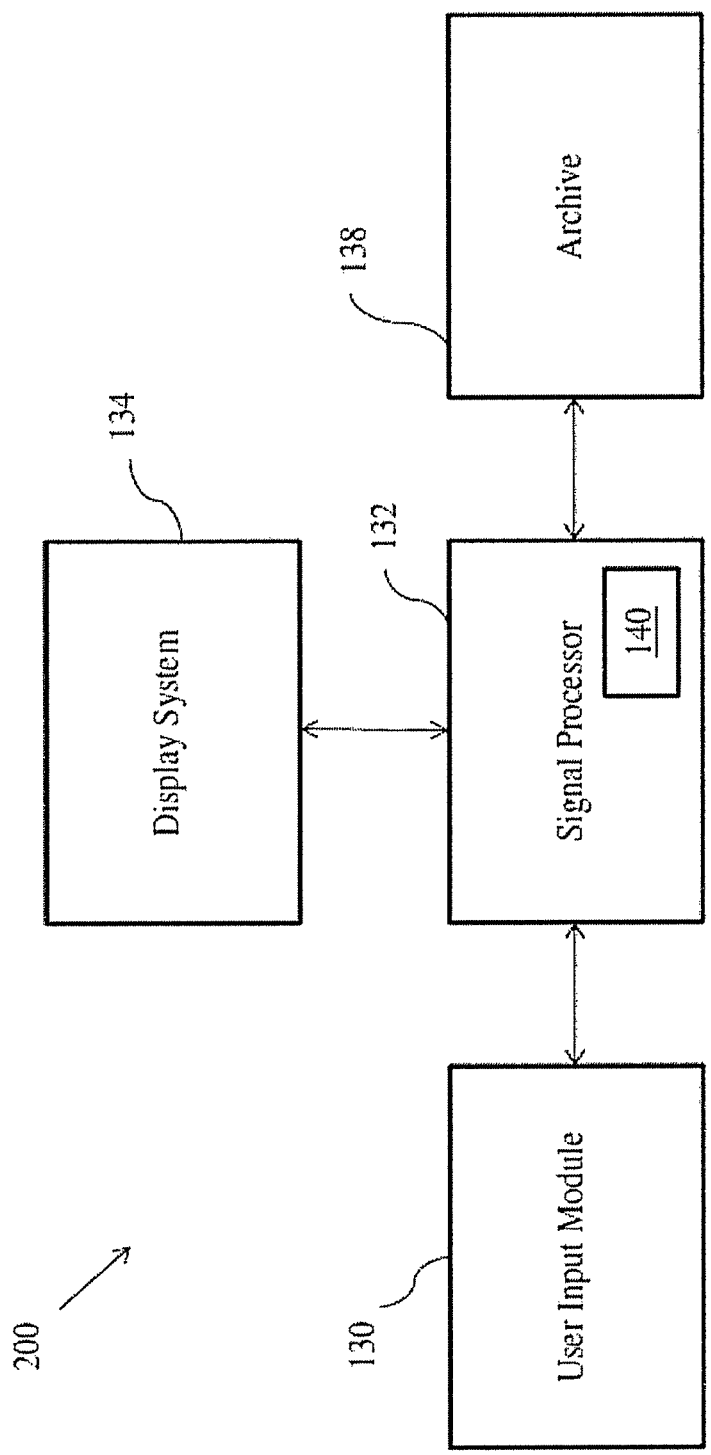
FIG. 2 is a block diagram of an exemplary medical workstation that is operable to provide enhanced visualization and navigation of 3D and 4D medical images by a dynamically configurable touch panel, in accordance with various embodiments.

FIG. 2 is a block diagram of an exemplary medical workstation 200 that is operable to provide enhanced visualization and navigation of 3D and 4D medical images by a dynamically configurable touch panel 130, in accordance with various embodiments. In various embodiments, components of the medical workstation 200 may share various characteristics with components of the ultrasound system 100, as illustrated in FIG. 1 and described above. Referring to FIG. 2, the medical workstation 200 comprises a display system 134, a signal processor 132, an archive 138, and a user input module 130, among other things. Components of the medical workstation 200 may be implemented in software, hardware, firmware, and/or the like. The various components of the medical workstation 200 may be communicatively linked. Components of the medical workstation 200 may be implemented separately and/or integrated in various forms. For example, the display system 134 and the user input module 130 may be integrated as a touchscreen display.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as medical images, or any suitable information.

The signal processor 132 may be one or more central processing units, microprocessors, microcontrollers, and/or the like. The signal processor 132 may be an integrated component, or may be distributed across various locations, for example. The signal processor 132 comprises an image manipulation module 140, as described above with reference to FIG. 1, and may be capable of receiving input information from a user input module 130 and/or archive 138, configuring the display system 134 and/or the user input module 130 based at least in part on a selected image display mode, generating an output displayable by a display system 134 and/or user input module 130, and manipulating the output in response to input information from a user input module 130, among other things. The signal processor 132 and/or image manipulation module 140 may be capable of executing any of the method(s) and/or set(s) of instructions discussed herein in accordance with the various embodiments, for example.

The archive 138 may be one or more computer-readable memories integrated with the medical workstation 200 and/or communicatively coupled (e.g., over a network) to the medical workstation 200, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores medical image data and instructions for configuring a touch panel 130 and manipulating medical image data based on user inputs at the touch panel 130, for example.

The user input module 130 may include any device(s) capable of communicating information from a user and/or at the direction of the user to the signal processor 132 of the medical workstation 200, for example. As discussed above with respect to FIG. 1, the user input module 130 may include a touch panel 410, 700, 800, button(s), a mousing device, keyboard, camera, voice recognition, and/or any other device capable of receiving a user directive.

Figure 9:
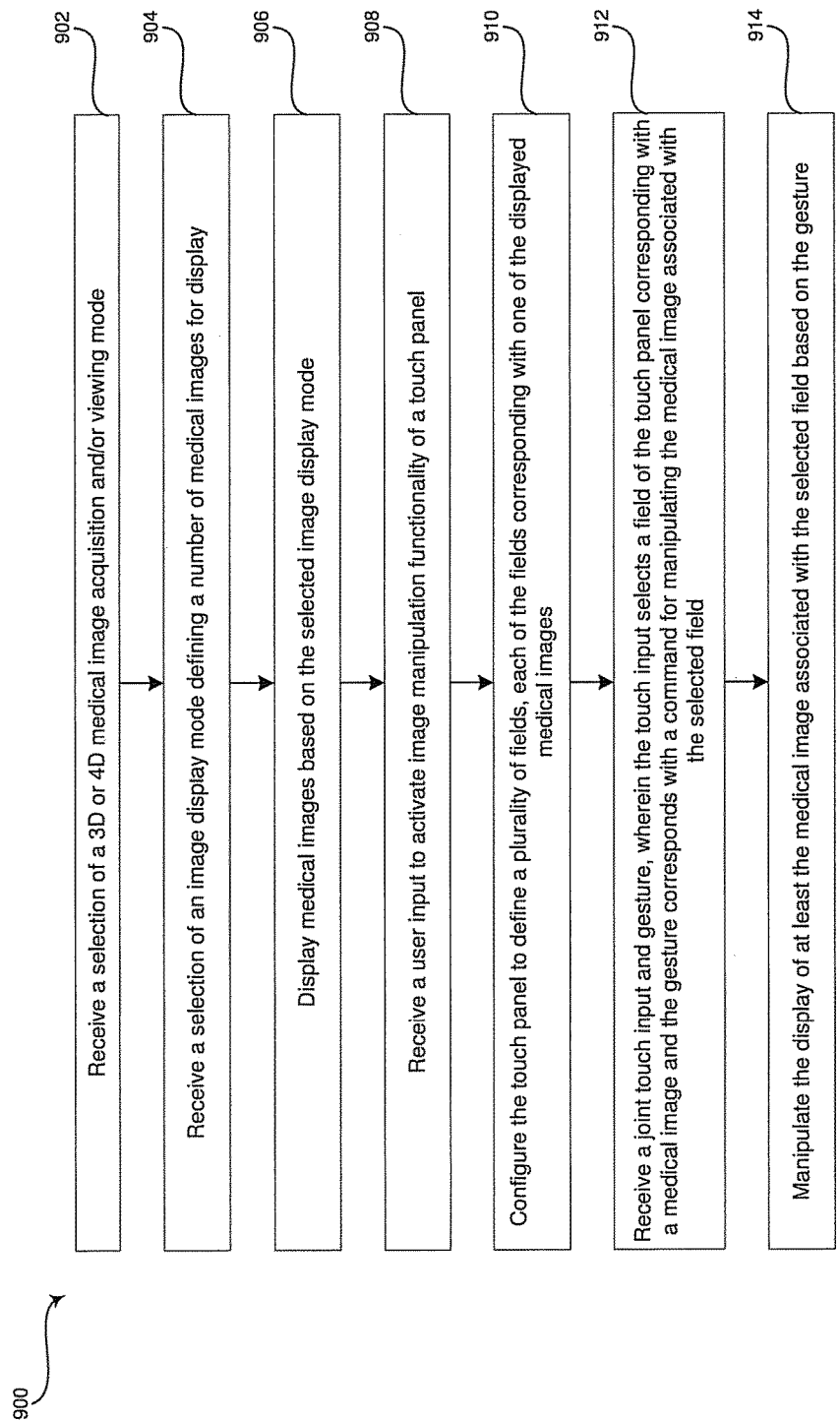
FIG. 9 is a flow chart illustrating exemplary steps that may be utilized for providing enhanced visualization and navigation of three dimensional (3D) and four dimensional (4D) medical images by a dynamically configurable touch panel, in accordance with various embodiments.

FIG. 9 is a flow chart illustrating exemplary steps that may be utilized for providing enhanced visualization and navigation of three dimensional (3D) and four dimensional (4D) medical images 510, 540, 610-640 by a dynamically configurable touch panel 130, 410, 700, 800, in accordance with various embodiments. Referring to FIG. 9, there is shown a flow chart 900 comprising exemplary steps 902 through 914. Certain embodiments of the present invention may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 902, the signal processor 132 may receive a selection of a 3D or 4D medical image acquisition and/or viewing mode from a user input module 130. For example, a medical device operator may select an acquisition/viewing mode button 340 on a medical device control panel 300. As another example, a medical workstation user may use a mousing device, keyboard, or touch panel 130 to select a 3D or 4D image set stored in an archive 138 for review. In response to the image acquisition and/or viewing mode selection, the signal processor 132 may activate and/or display various options or available functionality that accompanies the selected image acquisition and/or viewing mode. The options and available functionality may be provided at the display system 134 and/or the user input module 130.

At step 904, the signal processor 132 may receive a selection of an image display mode defining a number of medical images 510, 540, 610-640 for display. The image display mode may be a single image view mode, a dual-view mode 500, a quad-view mode 600, or any suitable display mode for presenting one or more medical images. For example, a medical device operator may select an image display mode button 330 on a medical device control panel 300. As another example, a medical workstation user may use a user input module 130 to select the display mode.

At step 906, the signal processor 132 may display medical images 510, 540, 610-640 at the display system 134 and/or a user input module 130 based at least in part on the image display mode selected at step 904. For example, the signal processor 132 may present the medical images 510, 540, 610-640 at the display system 134 in a dual-view mode 500 or a quad-view mode 600 as illustrated in FIGS. 5 and 6, respectively.

At step 908, the image manipulation module 140 of the signal processor 132 may activate image manipulation functionality of a touch panel 130, 410, 700, 800 in response to a user input provided at a user input module 130. For example, a medical device operator may depress a rotary encoder 320 of the medical device control panel 300, such as the X-rotation rotary encoder 320 or any suitable defined input, to launch the image manipulation functionality of the touch panel 130, 410, 700, 800. As another example, a medical workstation user may use a mousing device, keyboard, touch panel, or any suitable user input module 130 to activate the image manipulation functionality of the touch panel 130, 410, 700, 800. The touch panel user input device 130, 410, 700, 800 may have different functionality for different applications. The image manipulation module 140 of the signal processor 132 activates or switches from a previous touch panel configuration to the configuration associated with the image manipulation mode in response to the user input selecting the image manipulation functionality.

At step 910, the image manipulation module 140 of the signal processor 132 may configure the surface of the touch panel 130, 410, 700, 800 to define a plurality of fields 702, 708, 802-808 based at least in part on the image display mode selected at step 904. The plurality of fields 702, 708, 802-808 configured by the image manipulation module 140 each correspond with one of the medical images displayed at step 906. For example, the image manipulation module 140 may configure the touch panel 700 surface to define a first field 702 and a second field 708 separated by a dividing line 714 based at least in part on a dual-view mode 500 image display mode selection received at step 904. The first 702 and second 708 fields are configured by the image manipulation module 140 to correspond with first 510 and second 540 medical images, respectively, presented on the touch panel 700 and/or at a display system 134. As another example, the image manipulation module 140 may configure the touch panel 800 surface to define a first field 802, a second field 804, a third field 806, and a fourth field 808 separated by dividing lines 814 based at least in part on a quad-view mode 600 image display mode selection received at step 904. The first 802, second 804, third 806, and fourth 808 fields are configured by the image manipulation module 140 to correspond with first 610, second 620, third 630, and fourth 640 medical images, respectively, presented on the touch panel 800 and/or at the display system 134.

At step 912, the image manipulation module 140 of the signal processor 132 may receive a joint touch input and gesture provided at the touch panel 130, 410, 700, 800. The term "joint" refers to receiving both a touch input and at least one gesture provided at the surface of the touch panel 130, 410, 700, 800 without removing the input mechanism (e.g., finger(s) of a user, a stylus, etc.) from the surface of the touch panel 130, 410, 700, 800. The touch input portion of the joint input refers to the selection of a field 702, 708, 802-808 based on an initial position of the received input mechanism. The gesture portion of the joint input refers to the command for manipulating the image 510, 540, 610-640 corresponding with the selected field 702, 708, 802-808. In other words, the input information continues for as long as at least a portion of the input mechanism maintains contact with the surface of the touch panel 130, 410, 700, 800. Once contact is completely broken from the input surface of the touch panel 130, 410, 700, 800, any subsequent contact is considered a separate input.

For example, the image manipulation module 140 may receive a signal that an input mechanism, such as finger(s) of a user of a stylus, among other things, has made contact with the touch panel 410, 700, 800. The received input may cause the image manipulation module 140 to select a medical image 510, 540, 610-640 corresponding with the field 702, 708, 802-808 where the input was provided. The image manipulation module 140 may further receive a signal that the touch panel 410, 700, 800 has received a gesture 716, 816 while the input mechanism maintains contact with the surface of the touch panel 410, 700, 800. The gesture 716, 816 provided to the image manipulation module 140 from the touch panel 410, 700, 800 may correspond with a command for manipulating the selected image 510, 540, 610-640. As an example, a received gesture 716, 816 that slides left or right on the surface of the touch panel 410, 700, 800 may correspond with a command to manipulate the selected image 510, 540, 610-640 about the Y-axis. As another example, a received gesture 716, 816 that slides up or down on the surface of the touch panel 410, 700, 800 may correspond with a command to manipulate the selected image 510, 540, 610-640 about the X-axis.

In various embodiments, the image manipulation module 140 is configured to translate multi-touch gestures received at the touch panel 410, 700, 800. For example, a received gesture 716, 816 moving two fingers apart or together 716 may correspond with a command to zoom in or zoom out of the selected image 510, 540, 610-640. As another example, a received gesture 716, 816 moving two fingers in a circular motion 816 may correspond with a command to rotate the selected image 510, 540, 610-640 about the Z-axis. In an exemplary embodiment, the gesture input may extend into a neighboring field 702, 708, 802-808 of the touch panel 410, 700, 800 without changing the selection of the image 510, 540, 610-640. For example, after placing a finger in field 802 to select the first image 610 in the quad-view image display 600, a user may swipe their finger across into field 804 to rotate about the Y-axis or swipe down into fields 806 or 808 to rotate the selected image 610-640 about the X-axis. The user may remove the finger(s) or stylus from the surface of the touch panel 410, 700, 800 and provide an input at a different field 702, 708, 802-808 to select a different image 510, 540, 610-640 for manipulation.

At step 914, the image manipulation module 140 of the signal processor 132 may manipulate the display of at least the medical image 510, 540, 610-640 associated with the selected field 702, 708, 802-808 based on the gesture. As one example, in response to a user sliding the input mechanism left or right, the selected image 510, 540, 610-640 may be rotated about the Y-axis. Furthermore, other image manipulations, such as X-rotation, Z-rotation, zoom, parallel shift, dragging, and the like, may each be associated with a single-touch or multi-touch gesture. In various embodiments, the medical images 510, 540, 610-640 may be linked or otherwise associated such that rotation or other manipulation of the selected image 510, 610 also rotates or manipulates in unison the other displayed images 540, 620-640 in a corresponding manner based at least in part on the relationship between the selected image 510, 610 plane and the planes of the other images 620-640.

Aspects of the present invention provide a method 900 and system 100, 200 for providing enhanced visualization and navigation of three dimensional (3D) and four dimensional (4D) medical images by a dynamically configurable touch panel 130, 410, 700, 800. In accordance with various embodiments of the invention, the method 900 comprises receiving 904, by a processor 132 via a user input device 130, a selection of an image display mode 500, 600 defining a number of medical images 510, 540, 610-640 for display. The method 900 comprises configuring 910, by the processor 132, 140, a surface of a touch panel user input device 130, 410, 700, 800 to define a plurality of fields 702, 708, 802-808. Each of the plurality of fields 702, 708, 802-808 corresponds with a different one of the medical images 510, 540, 610-640. The method 900 comprises receiving 912, by the processor 132, 140 via the touch panel user input device 130, 410, 700, 800, an input 716, 816 that selects one of the plurality of fields 702, 708, 802-808 of the surface of the touch panel user input device 130, 410, 700, 800 and commands the processor 132, 140 to manipulate a medical image 510, 540, 610-640 corresponding with the selected one of the plurality of fields 702, 708, 802-808. The method 900 comprises manipulating 914, by the processor 132, 140 at one or more display devices 134, 410, 700, 800, at least the medical image 510, 540, 610-640 corresponding with the selected one of the plurality of fields 702, 708, 802-808 based at least in part on the input.

In various embodiments, the configuring the surface of the touch panel user input device 130, 410, 700, 800 is based at least in part on the image display mode 500, 600 selection. In a representative embodiment, the method 900 comprises displaying 906 the medical images 510, 540, 610-640 at the one or more display devices 134, 410, 700, 800 based at least in part on the selected image display mode 500, 600. In certain embodiments, the method 900 comprises acquiring the medical images 510, 540, 610-640 from one or more of a medical imaging device 100 and an archive 138. In various embodiments, the method 900 comprises receiving 902, by the processor 132 via the user input device 130, a selection of at least one of a three-dimensional (3D) and a four-dimensional (4D) image acquisition mode. The medical images 510, 540, 610-640 are acquired from the medical imaging device 100 based at least in part on the image acquisition mode selection.

In a representative embodiment, the method 900 comprises receiving 908, by the processor 132, 140 via the user input device 130, an input to activate image manipulation functionality of the touch panel user input device 130, 410, 700, 800. In certain embodiments, the user input device 130 that provides the input to activate image manipulation functionality of the touch panel user input device 130, 410, 700, 800 to the processor 132, 140 is a rotary encoder 320 of a medical imaging device control panel 300. The input is a depression of the rotary encoder 320. In various embodiment, the method 900 comprises displaying 910, at the touch panel user input device 130, 410, 700, 800, dividing lines 714, 814 that separate the plurality of fields 702, 708, 802-808 of the surface of the touch panel user input device 130, 410, 700, 800, and/or the different one of the medical images 510, 540, 610-640 in each of the corresponding plurality of fields 702, 708, 802-808.

In certain embodiments, the input 716, 816 that selects one of the plurality of fields 702, 708, 802-808 of the surface of the touch panel user input device 130, 410, 700, 800 and commands the processor 132, 140 to manipulate the medical image 510, 540, 610-640 corresponding with the selected one of the plurality of fields 702, 708, 802-808 is a joint touch input and gesture 716, 816 that is provided for a duration that an input mechanism is in contact with the surface of the touch panel user input device 130, 410, 700, 800. In various embodiments, the gesture 716, 816 is a multi-touch gesture.

In a representative embodiment, the medical images 510, 540, 610-640 are associated such that manipulation of the medical image 510, 540, 610-640 corresponding with the selected one of the plurality of fields 702, 708, 802-808 also manipulates in unison the other medical images 510, 540, 610-640 in a corresponding manner based at least in part on the relationship between a plane of the medical image 510, 540, 610-640 corresponding with the selected one of the plurality of fields 702, 708, 802-808 and planes of the other medical images 510, 540, 610-640. In certain embodiments, the selection of the image display mode 500, 600 is one of a dual-view mode 500 and a quad-view mode 600.

Various embodiments provide a system 100, 200 comprising a touch panel user input device 130, 410, 700, 800, one or more display devices 134, 410, 700, 800, and a processor 132. The touch panel user input device 130, 410, 700, 800 comprises a surface. The one or more display devices 134, 410, 700, 800 is operable to display medical images 510, 540, 610-640. The processor 132, 140 is configured to receive a selection of an image display mode 500, 600 defining a number of the medical images 510, 540, 610-640 for display. The processor 132, 140 is configured to configure the surface of the touch panel user input device 130, 410, 700, 800 based at least in part on the image display mode 500, 600 selection to define a plurality of fields 702, 708, 802-808. Each of the plurality of fields 702, 708, 802-808 corresponds with a different one of the medical images 510, 540, 610-640. The processor 132, 140 is configured to receive an input 716, 816 that selects one of the plurality of fields 702, 708, 802-808 of the surface of the touch panel user input device 130, 410, 700, 800 and commands the processor 132, 140 to manipulate a medical image 510, 540, 610-640 corresponding with the selected one of the plurality of fields 702, 708, 802-808. The processor 132, 140 is configured to manipulate at least the medical image 510, 540, 610-640 corresponding with the selected one of the plurality of fields 702, 708, 802-808 at the one or more display devices 134, 410, 700, 800 based at least in part on the input 716, 816.

In certain embodiments, the medical images 510, 540, 610-640 are displayed at the one or more display devices 134, 410, 700, 800 based at least in part on the selected image display mode 500, 600. The selection of the image display mode 500, 600 is one of a dual-view mode 500 and a quad-view mode 600. In a representative embodiment, the system 100, 200 comprises one or more of an archive 138 and a medical imaging device 100. The processor 132, 140 is configured to acquire the medical images 510, 540, 610-640 from the one or more of the archive 138 and the medical imaging device 100. In various embodiments, the processor 132, 140 is configured to receive an input and activate image manipulation functionality of the touch panel user input device 130, 410, 700, 800 in response to the received input.

In a representative embodiment, the one or more display devices 134, 410, 700, 800 is operable to display dividing lines 714, 814 that separate the plurality of fields 702, 708, 802-808 of the surface of the touch panel user input device 130, 410, 700, 800 and/or the different one of the medical images 510, 540, 610-640 in each of the corresponding plurality of fields 702, 708, 802-808. In certain embodiments, the input 716, 816 that selects one of the plurality of fields 702, 708, 802-808 of the surface of the touch panel user input device 130, 410, 700, 800 and commands the processor 132, 140 to manipulate the medical image 510, 540, 610-640 corresponding with the selected one of the plurality of fields 702, 708, 802-808 is a joint touch input and gesture 716, 816 that is provided for a duration that an input mechanism is in contact with the surface of the touch panel user input device 130, 410, 700, 800. In various embodiments, the medical images 510, 540, 610-640 are associated such that manipulation of the medical image 510, 540, 610-640 corresponding with the selected one of the plurality of fields 702, 708, 802-808 also manipulates in unison the other medical images 510, 540, 610-640 in a corresponding manner based at least in part on the relationship between a plane of the medical image 510, 540, 610-640 corresponding with the selected one of the plurality of fields 702, 708, 802-808 and planes of the other medical images 510, 540, 610-640.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing enhanced visualization and navigation of three dimensional (3D) and four dimensional (4D) medical images by a dynamically configurable touch panel.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
    receiving, by a processor via a user input device, a selection of an image display mode defining a number of medical images for display at one or more display devices;
    configuring, by the processor, a surface of a touch panel user input device to define a plurality of fields on the surface, wherein each of the plurality of fields corresponds with a different one of the medical images;
    receiving, by the processor via the touch panel user input device, an input on the surface of the touch panel user input device that selects one of the plurality of fields of the surface and commands the processor to manipulate a view of a medical image corresponding with the selected one of the plurality of fields, wherein the input is received after the configuring the surface of the touch panel user input device and is independent of the definition of the plurality of fields on the surface; and
    manipulating, by the processor at the one or more display devices, the view of at least the medical image corresponding with the selected one of the plurality of fields based at least in part on the input.

2. The method according to claim 1, wherein the configuring the surface of the touch panel user input device is based at least in part on the image display mode selection.

3. The method according to claim 1, comprising displaying the medical images at the one or more display devices based at least in part on the selected image display mode.

4. The method according to claim 1, comprising acquiring the medical images from one or more of a medical imaging device and an archive.

5. The method according to claim 4, comprising receiving, by the processor via the user input device, a selection of at least one of a three-dimensional (3D) and a four-dimensional (4D) image acquisition mode, and wherein the medical images are acquired from the medical imaging device based at least in part on the image acquisition mode selection.

6. The method according to claim 1, comprising receiving, by the processor via the user input device, an input to activate image manipulation functionality of the touch panel user input device.

7. The method according to claim 6, wherein the user input device that provides the input to activate image manipulation functionality of the touch panel user input device to the processor is a rotary encoder of a medical imaging device control panel, and wherein the input is a depression of the rotary encoder.

8. The method according to claim 1, comprising displaying, at the touch panel user input device, one or more of:
    dividing lines that separate the plurality of fields of the surface of the touch panel user input device, and
    the different one of the medical images in each of the corresponding plurality of fields.

9. The method according to claim 1, wherein the input that selects one of the plurality of fields of the surface of the touch panel user input device and commands the processor to manipulate the view of the medical image corresponding with the selected one of the plurality of fields is a joint touch input and gesture that is provided for a duration that an input mechanism is in contact with the surface of the touch panel user input device.

10. The method according to claim 9, wherein the gesture is a multi-touch gesture.

11. The method according to claim 1, wherein the medical images are associated such that manipulation of the view of the medical image corresponding with the selected one of the plurality of fields also manipulates in unison views of the other medical images in a corresponding manner based at least in part on the relationship between a plane of the medical image corresponding with the selected one of the plurality of fields and planes of the other medical images.

12. The method according to claim 1, wherein the selection of the image display mode is one of a dual-view mode and a quad-view mode.

13. A system, comprising:
    a touch panel user input device comprising a surface;
    one or more display devices operable to display medical images; and
    a processor configured to:
        receive a selection of an image display mode defining a number of the medical images for display at the one or more display devices, configure the surface of the touch panel user input device based at least in part on the image display mode selection to define a plurality of fields on the surface, wherein each of the plurality of fields corresponds with a different one of the medical images, receive an input on the surface of the touch panel user input device that selects one of the plurality of fields of the surface and commands the processor to manipulate a view of a medical image corresponding with the selected one of the plurality of fields, wherein the input is received after the surface of the touch panel user input device is configured, and wherein the input is independent of the definition of the plurality of fields on the surface, and manipulate the view of at least the medical image corresponding with the selected one of the plurality of fields at the one or more display devices based at least in part on the input.

14. The system according to claim 13, wherein the medical images are displayed at the one or more display devices based at least in part on the selected image display mode, and wherein the selection of the image display mode is one of a dual-view mode and a quad-view mode.

15. The system according to claim 13, comprising one or more of an archive and a medical imaging device, wherein the processor is configured to acquire the medical images from the one or more of the archive and the medical imaging device.

16. The system according to claim 13, wherein the processor is configured to receive an input and activate image manipulation functionality of the touch panel user input device in response to the received input.

17. The system according to claim 13, wherein the one or more display devices is operable to display one or more of:

dividing lines that separate the plurality of fields of the surface of the touch panel user input device, and the different one of the medical images in each of the corresponding plurality of fields.

18. The system according to claim 13, wherein the input that selects one of the plurality of fields of the surface of the touch panel user input device and commands the processor to manipulate the view of the medical image corresponding with the selected one of the plurality of fields is a joint touch input and gesture that is provided for a duration that an input mechanism is in contact with the surface of the touch panel user input device.

19. The system according to claim 13, wherein the medical images are associated such that manipulation of the view of the medical image corresponding with the selected one of the plurality of fields also manipulates in unison views of the other medical images in a corresponding manner based at least in part on the relationship between a plane of the medical image corresponding with the selected one of the plurality of fields and planes of the other medical images.

20. A non-transitory computer readable medium having stored thereon, a computer program having at least one code section, the at least one code section being executable by a machine for causing the machine to perform steps comprising:

receiving a selection of an image display mode defining a number of medical images for display at one or more display devices;

configuring a surface of a touch panel user input device to define a plurality of fields on the surface, wherein each of the plurality of fields corresponds with a different one of the medical images;

receiving an input on the surface of the touch panel user input device that selects one of the plurality of fields of the surface and commands the processor to manipulate a view of a medical image corresponding with the selected one of the plurality of fields, wherein the input is received after the configuring the surface of the touch panel user input device and is independent of the definition of the plurality of fields on the surface; and manipulating the view of at least the medical image corresponding with the selected one of the plurality of fields at the one or more display devices based at least in part on the input.

* * * * *